US008039101B2

(12) United States Patent
Reynaud et al.

(10) Patent No.: US 8,039,101 B2
(45) Date of Patent: Oct. 18, 2011

(54) RADIO-OPAQUE DENTAL PROSTHETIC MEMBER

(75) Inventors: Pierre-Luc Reynaud, Vaulnaveys le Haut (FR); Manh-Quynh Chu, Fontanil Cornillon (FR)

(73) Assignee: Societe de Recherches Techniques Dentaires-R.T.D., Saint Egreve (FR)

( * ) Notice: Subject to any disclaimer, the term of this patent is extended or adjusted under 35 U.S.C. 154(b) by 71 days.

(21) Appl. No.: 12/522,445

(22) PCT Filed: Jan. 18, 2008

(86) PCT No.: PCT/FR2008/050078
§ 371 (c)(1),
(2), (4) Date: Jul. 8, 2009

(87) PCT Pub. No.: WO2008/107596
PCT Pub. Date: Sep. 12, 2008

(65) Prior Publication Data
US 2010/0035214 A1 Feb. 11, 2010

(30) Foreign Application Priority Data

Jan. 19, 2007 (FR) ...................... 07 52751

(51) Int. Cl.
B32B 5/16 (2006.01)
A61C 13/30 (2006.01)
A61C 5/00 (2006.01)
A61C 5/04 (2006.01)
A61C 13/225 (2006.01)
A61K 6/08 (2006.01)

(52) U.S. Cl. .................. 428/331; 428/405; 428/407

(58) Field of Classification Search .................. 428/331, 428/405, 407; 427/405, 407
See application file for complete search history.

(56) References Cited

U.S. PATENT DOCUMENTS

| 3,493,403 | A | * | 2/1970 | Beck et al. ...................... 501/34 |
| 3,959,212 | A | * | 5/1976 | Rockett et al. ................ 523/117 |
| 4,350,532 | A | * | 9/1982 | Randklev .................... 106/31.95 |
| 4,503,169 | A | * | 3/1985 | Randklev ...................... 523/117 |
| 4,894,012 | A | * | 1/1990 | Goldberg et al. ............. 433/215 |
| 5,088,927 | A | * | 2/1992 | Lee ................................. 433/224 |
| 5,328,372 | A | * | 7/1994 | Reynaud et al. .............. 433/220 |
| 5,741,139 | A | * | 4/1998 | Sicurelli et al. ............... 433/220 |
| 5,890,904 | A | * | 4/1999 | Reynaud et al. .............. 433/220 |

(Continued)

FOREIGN PATENT DOCUMENTS

EP 399140 A2 * 11/1990

(Continued)

OTHER PUBLICATIONS

International Search Report dated Mar. 13, 2009, from corresponding PCT application.

*Primary Examiner* — James J Seidleck
*Assistant Examiner* — Peter A Salamon
(74) *Attorney, Agent, or Firm* — Young & Thompson

(57) ABSTRACT

The invention relates to a prefabricated radio-opaque dental prosthetic member made of a composite material that comprises fibers embedded in a resin, said resin containing at least one radio-opaque component, characterized in that the radio-opaque component consists of nanoparticles having a size lower than 50 nm in order to transmit a portion or the totality of the wavelengths ranging from 400 to 600 nm of an incident radiation.

20 Claims, 2 Drawing Sheets

U.S. PATENT DOCUMENTS

| | | | |
|---|---|---|---|
| 6,012,924 A * | 1/2000 | Reynaud et al. | 433/220 |
| 6,224,377 B1 * | 5/2001 | Bachmann et al. | 433/220 |
| 6,387,981 B1 * | 5/2002 | Zhang et al. | 523/117 |
| 6,413,638 B1 * | 7/2002 | Mager et al. | 428/403 |
| 6,899,948 B2 * | 5/2005 | Zhang et al. | 428/331 |
| 2003/0031985 A1 * | 2/2003 | Chu et al. | 433/225 |
| 2007/0208123 A1 * | 9/2007 | Kambe et al. | 524/432 |

FOREIGN PATENT DOCUMENTS

| | | |
|---|---|---|
| EP | 0 432 001 | 6/1991 |
| EP | 462512 A1 * | 12/1991 |
| EP | 0 793 474 | 9/1997 |
| EP | 1227781 A1 * | 8/2002 |
| EP | 1514850 A1 * | 3/2005 |
| EP | 1 227 781 | 9/2005 |
| EP | 1 586 294 | 10/2005 |
| EP | 1586294 A1 * | 10/2005 |
| FR | 2 874 498 | 3/2006 |
| FR | 2874498 A1 * | 3/2006 |
| GB | 2064550 A * | 6/1981 |
| GB | 2085012 A * | 4/1982 |
| GB | 2169906 A * | 7/1986 |
| WO | 96/15759 | 5/1996 |
| WO | WO 9626686 A1 * | 9/1996 |
| WO | WO 0108590 * | 2/2001 |
| WO | 01/30307 | 5/2001 |

* cited by examiner

RADIO-OPAQUE DENTAL PROSTHETIC MEMBER

This application is a 35 USC §371 national stage continuation of PCT/FR2008/050078, filed Jan. 18, 2008.

BACKGROUND OF THE INVENTION

1. Field of the Invention

The invention relates to a radio-opaque dental prosthetic member consisting of a composite material comprising longitudinal fibres such as glass fibres or quartz fibres embedded in a resin matrix.

In the rest of the description, the expression "prosthetic member" means a prefabricated composite material comprising longitudinal fibres embedded in a resin matrix for use in dentistry and in particular a dental post, an intradental post, a bridge reinforcement and preform for CAPC suitable for adhesion using a photopolymerizable or dual cement.

The invention is described more particularly in relation to dental posts made from composite material.

2. Description of the Related Art

Dental posts are used for the reconstruction of pulpless teeth. Two types of post are distinguished, respectively metal or ceramic posts, and composite posts.

Metal posts are generally made from stainless steel. They have the drawback of being subject to corrosion. Moreover, they have a different transverse elastic modulus from that of dentine, ultimately giving rise to detachment of the post.

To solve these problems, posts made from composite material have been proposed such as those described in particular in document EP-A-0 432 001 of the Applicant. These posts consist in practice of long fibres, of glass or carbon, embedded in a biocompatible thermoset resin matrix.

The essential drawback of the posts described in this document is that they are not radio-opaque to X-rays, making it difficult to locate them accurately at the time of their implant, but also in case of accidental ingestion.

To solve the problem of radio-opacity, document EP-A-0 793 474 proposes incorporating fillers based on metal oxide in the matrix, for example zirconium oxide. These fillers generally consist of micron-sized particles which effectively confer radio-opacity to the post, but which often form therewith aggregates generally having a size between 1 and 5 µm, increasing the viscosity of the resin and making its application difficult. Moreover, the volume occupied by the fillers represents a volume that is no longer available for the reinforcing fibres, commensurately decreasing the mechanical properties of the final material, mechanical properties which are nevertheless essential for the prosthetic members of the invention. Furthermore, the particles, the aggregates or their defects have comparable dimensions to the wavelengths of visible radiation. The light radiation issuing from the lamp for photopolymerization is therefore scattered when passing through the post, whose transparency to visible radiation is low. Furthermore, the non-uniform distribution of the aggregates in the post affects its aesthetic character.

Document FR-A-2 874 498 describes dental blocking members of composite material said to be transparent to light rays and comprising a matrix reinforced with fibres and containing radio-opaque particles, having a size close to a quarter of the wavelength of an incident radiation emitted by a photopolymerization lamp. In practice, the size of the radio-opaque particles is between 95 and 200 nm when the incident radiation wavelength is between 380 and 800 nm. Nothing is indicated concerning the usable types of radio-opaque particles. In fact, if for example zirconium oxide is used, a well-known radio-opaque component mentioned in document EP-A-0 793 474, having a size of about 100 nm, the incident radiation is not transmitted. Furthermore, even if the particle size is much lower than that of the metal oxides used in document EP-A-0 793 474, aggregates are still formed, and their presence in the matrix causes the same drawbacks as discussed above.

Document EP 1 227 781 A1 describes fibreless dental materials, and in particular cements and adhesives comprising a high proportion of silica nanoparticles (at least 40% by weight of the material), thereby providing a reasonably transparent material having satisfactory Theological properties in the uncrosslinked state (making the material easy to handle by the practitioner) and hard in the crosslinked state. The material may also contain radio-opaque heavy metal oxides, having a size close to 60 nm, whereof the surface is treated chemically to permit their absorption in the said material.

SUMMARY OF THE INVENTION

The Applicant has discovered quite surprisingly that reducing the size of the radio-opaque particles below 50 nm serves to ensure the transmission of all or part, generally at least 20% of an incident light radiation of which the spectrum contains the wavelengths for photopolymerizing the photopolymerizable cement. In practice, the wavelengths for photopolymerization are between 400 and 600 nm, usually between 400 and 530 nm. The invention relates to a prefabricated radio-opaque dental prosthetic member made of a composite material that comprises fibres imbedded in a resin, said resin containing at least one radio-opaque component. This prosthetic member is characterized in that the radio-opaque component consists of nanoparticles having a size lower than 60 nm, preferably lower than 50 nm, advantageously lower than 10 nm or even 5 nm, in order to transmit a portion or the totality of the wavelengths ranging from 400 to 600 nm of an incident radiation.

The invention relates more particularly to a dental post or an intradental post.

BRIEF DESCRIPTION OF THE DRAWING FIGURES

FIG. 1 shows the transmission spectrum of the compounds YF3, $YbF_3$, $Bi_2O_3$ and Au (thickness 10 microns for calculation) between 2 and 70 keV.

DETAILED DESCRIPTION OF THE INVENTION

According to a first feature, the radio-opaque component consists of a compound which has a very high absorption coefficient for the X-ray energies used (2-100 keV). For energies above the absorption thresholds, (K, L, M, etc.), the absorption coefficient is proportional to the density and to $Z_{eff}^4$ ($Z_{eff}=Z_{effective}$ corresponds to the effective atomic number of the material which depends on the atomic numbers of the chemical elements present in the material). On the contrary, in the energy ranges corresponding to the various absorption thresholds, the absorption displays wide fluctuations.

Figure 1:
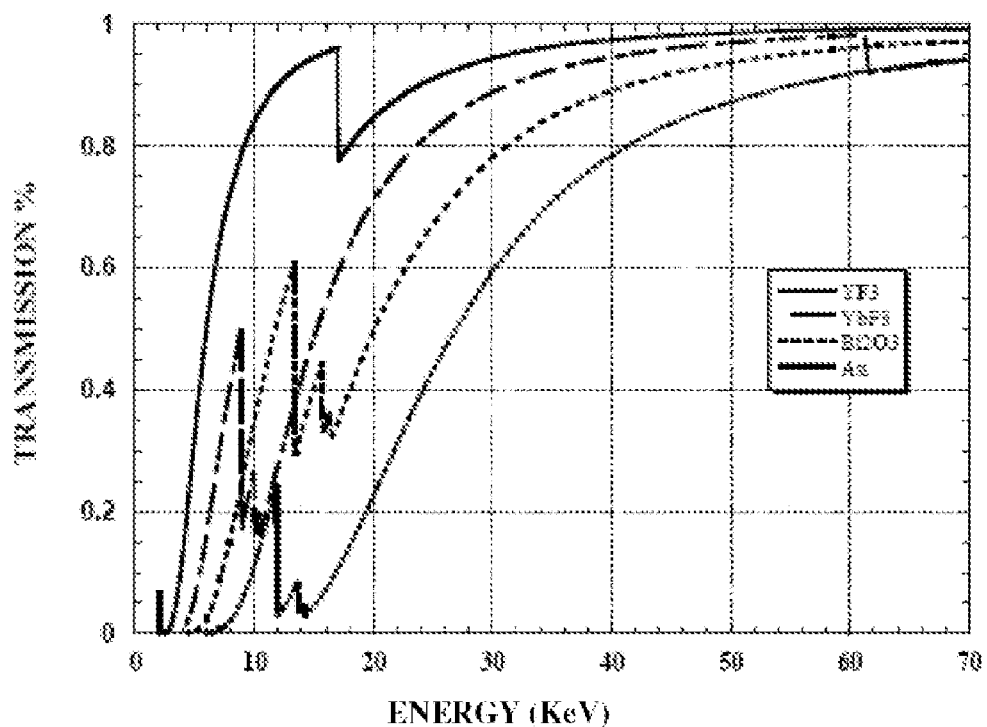

By way of example, FIG. 1 shows the transmission spectrum of the compounds $YF_3$, $YbF_3$, $Bi_2O_3$ and Au (thickness 10 microns for calculation) between 2 and 70 keV. High absorption jumps may be observed (drop in transmission) for particular energies, associated with the presence of the absorption thresholds of the chemical elements of the compounds considered.

Accordingly, the X-ray energy used determines the choice of the radio-opaque components. In general, elements having a high Z are preferably selected, of which the absorption thresholds are adapted to the X-ray energy to be absorbed. Within this family, high density materials are preferred. Toxic compounds are excluded.

In practice, the radio-opaque component is selected from the group comprising zinc oxide, yttrium oxide, zirconium oxide, tin oxide, barium sulphate, certain lanthanide oxides (for example ytterbium oxide), tantalum oxide, hafnium oxide, cerium oxide, tungsten oxide, bismuth oxide, bismuth oxycarbonate, alone or in mixtures thereof. Nanometer-sized metal fillers (gold) are not excluded. The advantageous chemical elements for the invention (X-ray absorption) can be used alone, (for example gold) or in combination with other chemical elements, for example in the form of pre-defined compounds ($BaZrO_3$, $MgWO_4$) or of a core/shell system. For each element, it is also possible to replace the oxide anions associated with the cations, by anions selected from the group comprising fluoride, carbonate, vanadate, sulphate, phosphate anions (for example ytterbium fluoride).

Advantageously, the radio-opaque component is selected from the group comprising zirconium oxide ($ZrO_2$), barium sulphate ($BaSO_4$), ytterbium fluoride ($YbF_3$), ytterbium oxide ($Yb_2O_3$), bismuth oxide ($Bi_2O_3$) and tin oxide ($SnO_2$).

In general, for a given radiation transmission percentage, in particular in the visible range, the higher the size of the nanometer-sized particles, the lower the proportion of nanoparticles in the prosthetic member. In practice, the proportion of nanoparticles in the prosthetic member accounts for between 1 and 30% by weight advantageously between 3 and 20% by weight.

With regard to the zirconium oxide, the Applicant has found that it transmitted:
  at least 20% of the incident rays having wavelengths between 400 and 600 nm with a nanoparticle size lower than 25 nm,
  at least 50% of the incident rays having wavelengths between 400 and 600 nm with a nanoparticle size lower than 20 nm, in fact between 5 and 20 nm.

In a particular embodiment, the zirconium oxide nanoparticles have a size lower than 12 nm, in practice between 8 and 12 nm, advantageously about 10 nm and preferably accounting for between 3 and 15% by weight of the prosthetic member. Such a combination is more particularly suitable for the preparation of dental or intradental posts.

With regard to barium sulphate, the Applicant has found that it transmitted at least 50% of the incident rays having a wavelength between 400 and 600 nm with a nanoparticle size lower than 50 nm.

In a particular embodiment, the barium sulphate nanoparticles have a size lower than 35 nm, in practice between 25 and 32 nm, advantageously about 30 nm and accounting for between 5 and 30% by weight of the prosthetic member. Such a combination is more particularly suitable for preparing dental or intradental posts.

With regard to bismuth oxide, the Applicant has found that it transmitted:
  at least 20% of the incident rays having wavelengths between 400 and 600 nm with a nanoparticle size lower than 25 nm,
  at least 50% of the incident rays having wavelengths between 400 and 600 nm with a nanoparticle size lower than 18 nm, in fact between 5 and 18 nm.

In a particular embodiment, the bismuth oxide nanoparticles have a size lower than 10 nm, in practice between 7 and 10 nm, advantageously about 8 nm and preferably accounting for between 2 and 15% by weight of the prosthetic member. Such a combination is more particularly suitable for preparing dental or intradental posts.

With regard to the tin oxide, the Applicant has found that it transmitted:
  at least 20% of the incident rays having wavelengths between 400 and 600 nm with a nanoparticle size lower than 27 nm,
  at least 50% of the incident rays having wavelengths between 400 and 600 nm with a nanoparticle size lower than 20 nm, in fact between 10 and 20 nm.

In a particular embodiment, the tin oxide nanoparticles have a size lower than 15 nm, in practice between 11 and 15 nm, advantageously about 13 nm and preferably accounting for between 3 and 20% by weight of the prosthetic member. Such a combination is more particularly suitable for preparing dental or intradental posts.

With regard to the ytterbium oxide, the Applicant has found that it transmitted:
  at least 20% of the incident rays having wavelengths between 400 and 600 nm with a nanoparticle size lower than 25 nm,
  at least 50% of the incident rays having wavelengths between 400 and 600 nm with a nanoparticle size lower than 20 nm, in fact between 5 and 20 nm.

In a particular embodiment, the ytterbium oxide nanoparticles have a size lower than 20 nm, in practice between 16 and 20 nm, advantageously about 18 nm and preferably accounting for between 2 and 15% by weight of the prosthetic member. Such a combination is more particularly suitable for preparing dental or intradental posts.

With regard to the ytterbium fluoride, the Applicant has found that it transmitted:
  at least 60% of the incident rays having a wavelength between 400 and 600 nm with a nanoparticle size lower than 50 nm,
  at least 90% of the incident rays having wavelengths between 400 and 600 nm with a nanoparticle size lower than 35 nm.

In a particular embodiment, the ytterbium fluoride nanoparticles have a size lower than 35 nm, in practice between 25 and 35 nm, advantageously about 30 nm and preferably accounting for between 3 and 20% by weight of the prosthetic member. Such a combination is more particularly suitable for preparing dental or intradental posts.

To improve the dispersion of the radio-opaque nanoparticles in the matrix and to prevent the salting out in the organism after implantation of the prosthetic member, they advantageously, prior to their incorporation in the resin, undergo a surface treatment also designated as "functionalization". This treatment corresponds to the grafting of organic or organometallic molecules having at least one chemical group suitable for reacting with the surface of the nanoparticle, and at least one chemical group capable of reacting with the components of the resin, advantageously by polymerization.

Furthermore and according to another feature, the two categories of chemical groups are separated by a molecular chain called "spacer group", in order to optimize the functionalization of the nanoparticles, promote the incorporation of the nanoparticles in the monomer solution, and more generally to control the properties of the matrix (physicochemical properties according to the length of this spacer and the nature of the substituents).

In other words, functionalization consists in grafting on the nanoparticle a chemical molecule having a C-R-F type of structure in which:

C is a function for bonding the molecule to the surface of the nanoparticle,

R is a spacer group, and

F is a group capable of reacting with the components of the matrix, advantageously by polymerization at the time of the crosslinking of the resin, and thereby ensuring the effective bonding of the nanoparticle in the matrix without any risk of salting out.

It should be noted that the size of the nanoparticles referred to is the size before surface treatment.

As a C group, use can be made for example of a complexing function of the surface cations of the nanoparticles. In the particular case of particles of chalcogenides, oxides or metals, the complexing function of the surface cations of the particles corresponding to the C group is for example a thiol, phosphine, phosphonate or carboxylate function. The complexing force of the C group must however be sufficient to ensure a higher rate of coverage of grafted molecules, particularly in the case in which this molecule substitutes for the one used during the synthesis of the nanoparticle as such. This complexing force may in particular be considerably reinforced by the use of polydentate ligands, such as dithiols and phosphine oligomers.

As a R group, use can be made of any spacer known to a person skilled in the art and typically a linear or branch $C_1$-$C_{10}$ alkyl group, such as —($CH_2$)—, —($C_2H_4$)—, —($C_3H_6$)—, —($C_4H_8$)— or an aromatic group like —($C_6H_4$)— or a combination thereof, which can be interrupted by one or more heteroatoms selected from O, N, S or P.

As a F group, use can be made of the groups selected from the group comprising epoxy, methacrylate, acrylate or any other polymerizable group compatible with the type of matrix used.

Use can also be made of groups reacting with the monomers of the matrix without necessarily being engaged in a polymerization reaction.

In an advantageous embodiment, the C-R-F grafting molecule is a polymerizable silane. The control of the hydrolysis-condensation reactions accordingly serves to coat the particles with a fine layer of silica, leaving a fraction of the polymerizable F functions accessible to the outside and hence to the components of the matrix. One of the advantages of this method is that the layer obtained around the particle serves to make a large number of F functional groups available.

Other grafting techniques can also be considered, for example such as direct coating of nanoparticles by organic polymers carrying both C groups and F groups.

In all cases, it should be noted that the functionalization of the particles leads to a modification of their surface state which may lead to destabilization of the colloidal solution in which the molecules are dispersed. The functionalization or grafting step must therefore obey a compromise between the optimization of the number of functional groups grafted and the stabilization of the particles in the dispersion medium.

According to the invention, the grafted molecule, as already stated, contains a spacer group R for reinforcing the particle dispersion forces in the case in which they are weakened by the chemical nature of the F function.

In an advantageous embodiment of the invention, the grafted molecule is selected from the group comprising:

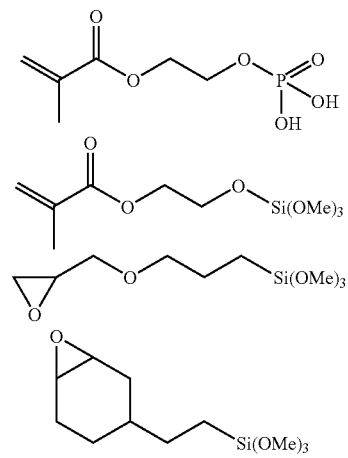

The radio-opaque nanoparticles may also consist of a "core/shell" type system.

In a first embodiment, the system contains:

a crystallized core containing at least one radio-opaque compound selected from the group comprising zinc oxide, yttrium oxide, zirconium oxide, tin oxide, barium sulphate, certain oxides of lanthanides (such as ytterbium oxide for example), tantalum oxide, tungsten oxide, bismuth oxide, bismuth oxycarbonate, hafnium oxide, cerium oxide, oxide anions which can be substituted by anions selected from the group comprising fluoride, carbonate, vanadate, sulphate, phosphate anions; metallic nanometer-sized fillers such as for example gold, alone or in combination and, more generally, a compound containing an advantageous chemical element for the invention (high X-ray absorption) used alone (gold for example) or in combination with other chemical elements, a first optional radio-opaque hybrid (organic-inorganic) shell prepared from a precursor of silica and alkoxysilanes, the alkoxysilanes carrying at least one radio-opaque element, advantageously iodine, a second shell containing silica.

Preferably, the crystallized core contains at least one radio-opaque compound selected from the group comprising zirconium oxide, barium sulphate, ytterbium oxide, bismuth oxide, tin oxide and ytterbium fluoride.

Advantageously, the alkoxysilanes carrying at least one radio-opaque element are the following molecules:

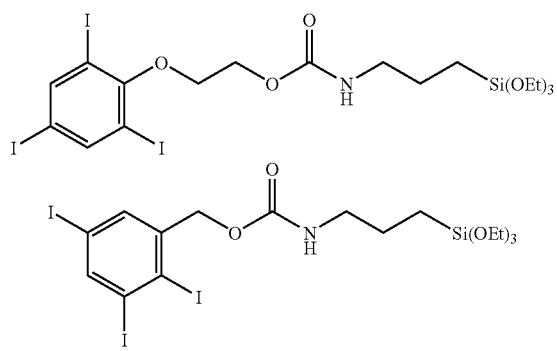

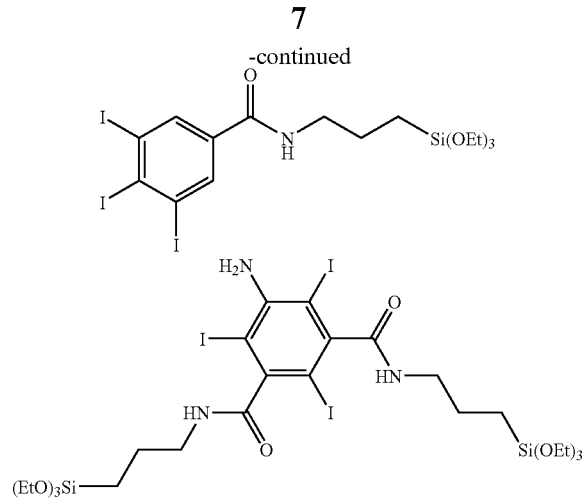

In a second embodiment, the system contains:
an amorphous core consisting of silica,
a first radio-opaque hybrid (organic-inorganic) shell prepared from a precursor of silica and alkoxysilanes, the alkoxysilanes carrying at least one radio-opaque element, advantageously bismuth, gadolinium, ytterbium or iodine,
a second shell containing silica.

Regardless of the core/shell system adopted, it advantageously undergoes a surface treatment before its incorporation in the matrix, consisting in incorporating in a second shell, using at least one functionalized alkoxysilane, a function for polymerizing with the resin. In practice, the system is obtained by the application to the crystallized core of a hybrid (organic-inorganic) shell prepared from a precursor of silica and alkoxysilane having a function for polymerizing with the resin.

The synthesis of the nanoparticles is well known and more particularly described in documents 1 to 8. These references are given as examples and are not limiting.

The incorporation of the nanoparticles in the resin matrix is advantageously carried out using a colloidal solution of these nanoparticles in a solvent or a solvent mixture compatible with the monomer or monomers of the matrix (acrylic or methacrylic monomer, for example such as methylmethacrylate (MMA), hexanedioldimethacrylate (HEDMA) or 1,4-butanedioldimethacrylate (BDDMA)). The solvent is then removed by techniques known to a person skilled in the art (evaporation under vacuum, exchange by dialysis, etc.). This step must not cause the destabilization of the new colloidal solution. This step is followed by the polymerization step.

In practice, the nanoparticles account for between 20 and 50% by weight of the resin, or 1 to 30% by weight of the post.

With regard to the fibres, there may be glass fibres or quartz fibres which are optionally radio-opaque. In general, depending on the manufacturing process, they account for between 55 and 70% by volume of the prosthetic member.

The prosthetic members of the invention can be obtained by any technique known to a person skilled in the art, in particular by pultrusion. This technology is used to form rods based on longitudinal fibres embedded in the resin, which is crosslinked during the process. The rods are then machined. The incorporation of the nanoparticles in the resin is carried out by the methods described above.

The invention and the advantages thereof clearly appear from the following exemplary embodiment.

Figure 2:
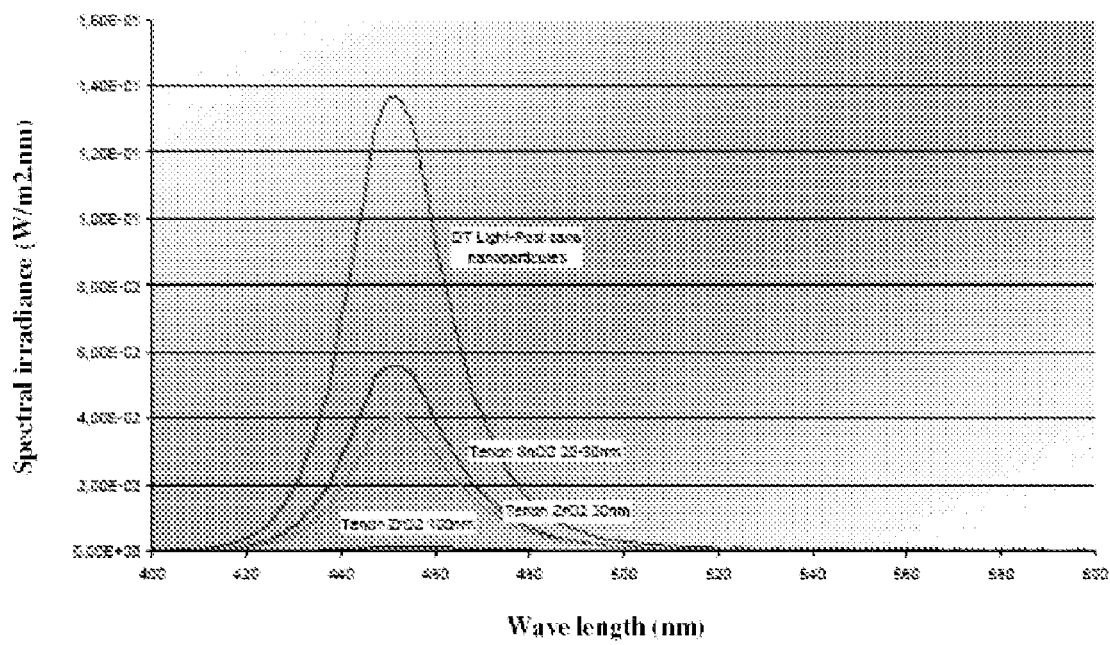
FIG. 2 is a graphic representation of the spectral irradiance of several posts through an LED lamp.

FIG. 2 is a graphic representation of the spectral irradiance of several posts through an LED lamp.

Figure 3:
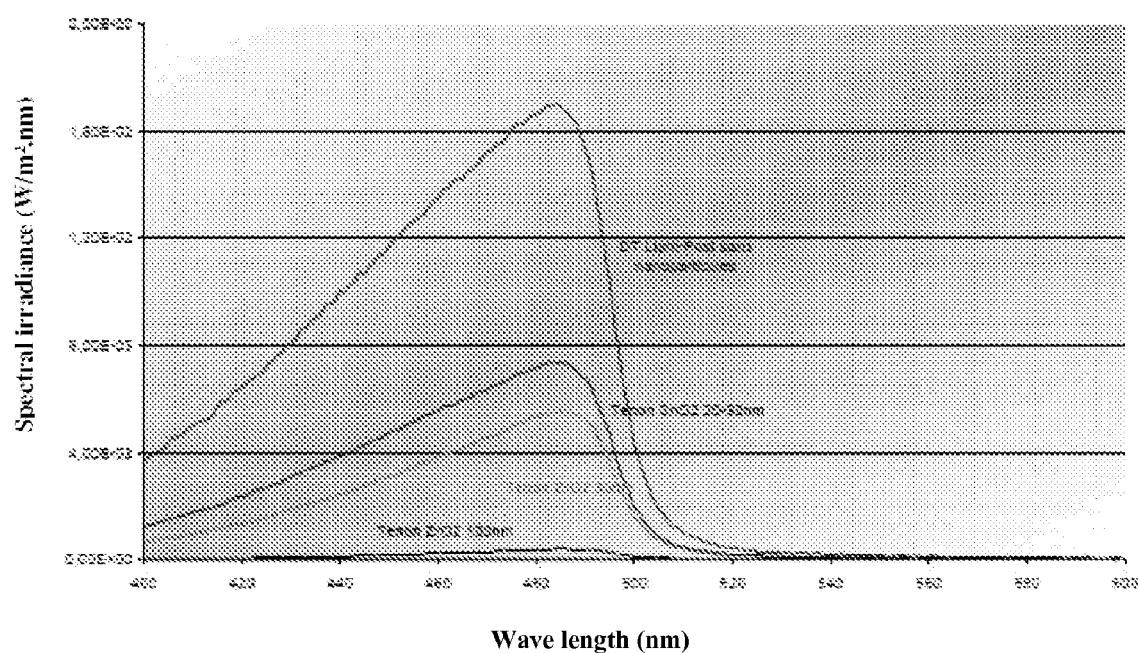
FIG. 3 is a graphic representation of the spectral irradiance of several posts through a halogen lamp.

FIG. 3 is a graphic representation of the spectral irradiance of several posts through a halogen lamp.

A colloidal solution of zirconium oxide ($ZrO_2$) nanoparticles having a size close to 30 nm is dispersed in an epoxy resin matrix. The concentration of dry nanoparticles in the resin matrix is 23% by weight. The solvent, ethanol, is separated from the mixture by evaporation. A second solution of zirconium oxide nanoparticles having a size close to 100 nm and a third solution of tin oxide ($SnO_2$) nanoparticles having a size of 20-30 nm are prepared in the same way. The nanoparticle concentration is identical for the three resin matrices.

Three posts are prepared from these three resin matrices with radio-opaque fibres. The fibres account for 62% by volume of the post. The shape of the posts corresponds to that of the DT Light-Post® (RTD) posts. The properties in terms of radio-opacity and photo-polymerizable light transmission are evaluated taking account of the DT Light-Post® post as a reference without nanoparticles in the matrix.

The radio-opacity is evaluated by the procedure of standard ISO 4049.

The following results are obtained:
DT Light-Post® post: 2.44 mm equivalent Al/mm material
Post containing nanoparticles ($ZrO_2$) 100 nm: 2.88 mm equ. Al/mm material
Post containing nanoparticles ($ZrO_2$) 30 nm: 2.91 mm equ. Al/mm material
Post containing nanoparticles ($SnO_2$) 20-30 nm: 3.24 mm equ. Al/mm material The light transmission is evaluated by spectral irradiance measurements. The energy transmitted by a photopolymerization lamp through the post is measured in an integrating sphere. This spectral irradiance expressed in $W/m^2 \cdot nm$ and the maximum transmitted wavelength peak are measured for each type of post. The MiniLED® (SATELEC) lamp was employed with a power of 1000 $mW/cm^2$. The results are summarized in the table below.

|  | Spectral irradiance $W/m^2 \cdot nm$ | Maximum peak $W/m^2 \cdot nm$ |
| --- | --- | --- |
| DT Light-Post ® | 3.93 | $1.37 \cdot 10^{-1}$ |
| Post nanoparticles ($ZrO_2$) 100 nm | 0.045 | $1.37 \cdot 10^{-3}$ |
| Post nanoparticles ($ZrO_2$) 30 nm | 1.19 | $3.99 \cdot 10^{-2}$ |
| Post nanoparticles ($SnO_2$) 20-30 nm | 1.63 | $5.57 \cdot 10^{-2}$ |

Thus these experimental results show that the transmission of light in a material containing 30 nm zirconia nanoparticles is 30% and 40% for tin oxide in comparison with the transmission through a material without nanoparticles. When the size of the nanoparticle is 100 nm, as in the case of zirconia, the proportion of light transmitted is close to zero (exactly 1%). This observation is valid for the spectral irradiance or the maximum peak.

The wavelength transmitted through the post is 450 nm.

The same experiment is conducted with a VIP® (BISCO) halogen lamp.

|  | Spectral irradiance $W/m^2 \cdot nm$ | Maximum peak $W/m^2 \cdot nm$ |
| --- | --- | --- |
| DT Light-Post ® | 1.11 | $1.7 \cdot 10^{-2}$ |
| Post nanoparticles ($ZrO_2$) 100 nm | $1.99 \cdot 10^{-2}$ | $3.96 \cdot 10^{-4}$ |
| Post nanoparticles ($ZrO_2$) 30 nm | $3.15 \cdot 10^{-1}$ | $5.57 \cdot 10^{-3}$ |
| Post nanoparticles ($SnO_2$) 20-30 nm | $4.54 \cdot 10^{-1}$ | $7.39 \cdot 10^{-3}$ |

The light transmission through the material containing the zirconium oxide nanoparticles having a size of 30 nm is 30% and 40% for tin oxide. It is close to zero for the zirconium oxide nanoparticles having a size of 100 nm. The maximum wavelength is 485 nm.

The advantages of the invention clearly appear from the above description. In particular, the presence of nanoparticles having a size lower than 50 nm serves to have a transparent prosthetic member in the visible range, which is radio-opaque to X-rays and aesthetically suitable.

REFERENCES

1/ Synthesis of Barium Sulfate nanoparticles in Water-in-Oil Microemulsion Systems, Colloid Journal, Vol. 63, No. 6, 2001, pp. 714-717.
2/ Quantum-sized PbS, CdS, Ag2S, Sb2S3 and Bi2S3 particles as sensitizers for various nanoporous wide-bandgap semiconductors, The Journal of Physical Chemistry, Vol. 98, No. 12, 1994, 3183.
3/ Transparent colloidal solution of 2 nm ceria particles, Chem. Commun., 1999, 957-958.
4/ Multigram Scale Synthesis and Characterization of Monodisperse Tetragonal Zirconia Nanocrystals, J. Am. Chem. Soc. 2003, 125, 6553-6557.
5/ Nanostructured oxide coatings via emulsion precipitation, Theses Fiona C. M. Woudenberg, Twente University (Netherlands) (2001).
6/ One-pot synthesis of YF$_3$@silica core/shell nanoparticles, Chem. Commun., 2006, 776-778.
7/ Solvothermal reaction of rare-earth metals in 2-methoxyethanol and 2-aminoethanol, J. Am. Ceram. Soc., 89 [4] 1205-1211 (2006).
8/ Bismuth titanate nanoparticles dispersed polyacrylates, J. Mater. Res., Vol. 19, No. 8 (2004) 2343.

The invention claimed is:
1. A prefabricated radio-opaque dental prosthetic member, comprising:
    a composite material that comprises fibres embedded in a resin, said resin containing at least one radio-opaque component consisting of barium sulphate nanoparticles having a size between 25 and 32 nm and accounting for between 5 and 30% of the prosthetic member, in order to transmit a portion or the totality of the wavelengths ranging from 400 to 600 nm of an incident radiation.
2. A prefabricated radio-opaque dental prosthetic member, comprising:
    a composite material that comprises fibres embedded in a resin, said resin containing at least one radio-opaque component consisting of nanoparticles of ytterbium fluoride (YbF$_3$) having a size lower than 50 nm in order to transmit a portion or a totality of the wavelengths ranging from 400 to 600 nm of an incident radiation.
3. A prefabricated radio-opaque dental prosthetic member, comprising:
    a composite material that comprises fibres embedded in a resin, said resin containing at least one radio-opaque component consisting of nanoparticles of ytterbium fluoride (YbF$_3$) having a size lower than 35 nm, and accounting for between 3 and 20% by weight of the prosthetic member.
4. The prosthetic member according to claim 1, wherein the radio-opaque component undergoes a surface treatment consisting of a grafting of an organic or organometallic molecule having at least one chemical group suitable for reacting with a surface of the nanoparticle, and at least one chemical group capable of polymerizing with the resin, the two chemical groups being separated by a molecular chain.

5. The prosthetic member according to claim 4, wherein the molecule grafted on the nanoparticle is selected from the group consisting of

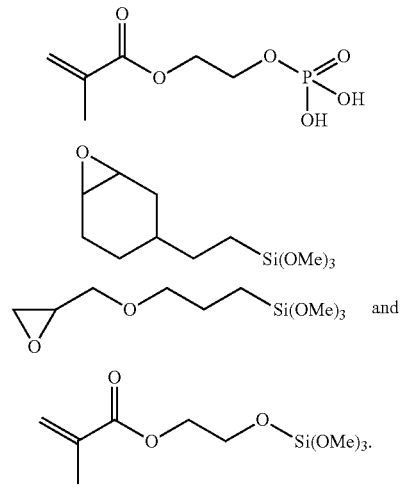

6. The prosthetic member according to claim 4, wherein the chemical group suitable for reacting with the surface of the nanoparticle is a complexing function of surface cations of the nanoparticle selected from the group consisting of thiol, phosphine, phosphonate and carboxylate moieties.

7. The prosthetic member according to claim 4, wherein the molecular chain separating the two chemical groups is selected from the group consisting of a linear or branched $C_1$-$C_{10}$ alkyl group, an aromatic group and a combination of these groups optionally interrupted by one or more heteroatoms selected from O, N, S or P.

8. The prosthetic member according to claim 4, wherein the chemical groups capable of polymerizing with the resin are selected from the group consisting of epoxy, methacrylate and acrylate.

9. The prosthetic member according to claim 4, wherein the grafted molecule is a polymerizable silane.

10. The prosthetic member according to claim 1, wherein the prosthetic member is a dental or intradental post.

11. The prosthetic member according to claim 3, wherein the nanoparticles of ytterbium fluoride (YbF$_3$) have a size between 25 and 35 nm.

12. The prosthetic member according to claim 3, wherein the nanoparticles of ytterbium fluoride (YbF$_3$) have a size of about 30 nm.

13. The prosthetic member according to claim 2, wherein the radio-opaque component undergoes a surface treatment consisting of a grafting of an organic or organometallic molecule having at least one chemical group suitable for reacting with a surface of the nanoparticle, and at least one chemical group capable of polymerizing with the resin, the two chemical groups being separated by a molecular chain.

14. The prosthetic member according to claim 13, wherein the molecule grafted on the nanoparticle is selected from the group consisting of

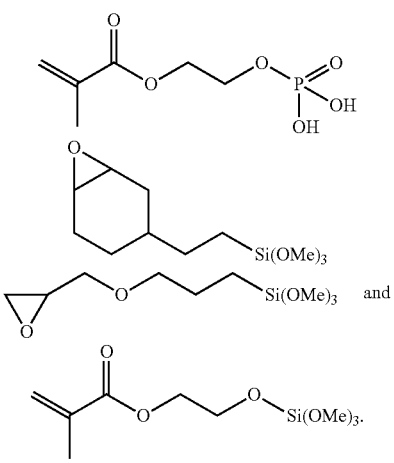

and

15. The prosthetic member according to claim 13, wherein the chemical group suitable for reacting with the surface of the nanoparticle is a complexing function of surface cations of the nanoparticle selected from the group consisting of thiol, phosphine, phosphonate and carboxylate moieties.

16. The prosthetic member according to claim 13, wherein the molecular chain separating the two chemical groups is selected from the group consisting of a linear or branched $C_1$-$C_{10}$ alkyl group, an aromatic group and a combination of these groups optionally interrupted by one or more heteroatoms selected from O, N, S or P.

17. The prosthetic member according to claim 3, wherein the radio-opaque component undergoes a surface treatment consisting of a grafting of an organic or organometallic molecule having at least one chemical group suitable for reacting with a surface of the nanoparticle, and at least one chemical group capable of polymerizing with the resin, the two chemical groups being separated by a molecular chain.

18. The prosthetic member according to claim 17, wherein the molecule grafted on the nanoparticle is selected from the group consisting of

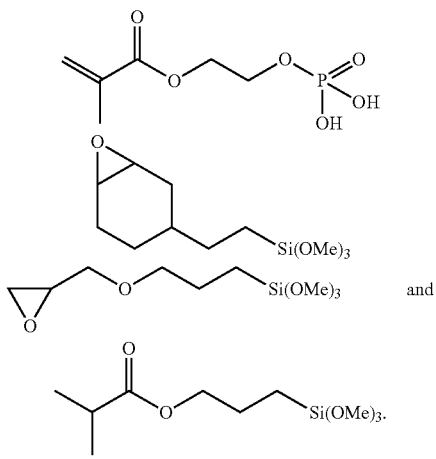

and

19. The prosthetic member according to claim 17, wherein the chemical group suitable for reacting with the surface of the nanoparticle is a complexing function of surface cations of the nanoparticle selected from the group consisting of thiol, phosphine, phosphonate and carboxylate moieties.

20. The prosthetic member according to claim 17, wherein the molecular chain separating the two chemical groups is selected from the group consisting of a linear or branched $C_1$-$C_{10}$ alkyl group, an aromatic group and a combination of these groups optionally interrupted by one or more heteroatoms selected from O, N, S or P.

* * * * *